United States Patent
Gembus et al.

(10) Patent No.: US 9,416,114 B2
(45) Date of Patent: Aug. 16, 2016

(54) 1,2,4-TRIAZINE DERIVATIVES FOR THE TREATMENT OF VIRAL INFECTIONS

(71) Applicants: CENTRE NATIONAL DE LA RECHERCHE SCIENTIFIQUE (CNRS), Paris (FR); UNIVERSITE DE ROUEN, Mont Saint Aignan (FR); INSTITUT NATIONAL DES SCIENCES APPLIQUEES DE ROUEN (INSA), Saint Etienne du Rouvray (FR)

(72) Inventors: Vincent Gembus, Rouen (FR); Philippe Jubault, Preaux (FR); Christophe Hoarau, Bois Guillaume (FR); Vincent Levacher, Fontaine-sous-Preaux (FR); Jean-Francois Bonfanti, Issy les Moulineaux (FR); David Graig McGowan, Beerse (BE); Jerome Emile Georges Guillemont, Isse les Moulineaux (FR)

(73) Assignees: CENTRE NATIONAL DE LA RECHERCHE SCIENTIFIQUE (CNRS), Paris (FR); UNIVERSITE DE ROUEN, Mont Saint Aignan; INSTITUT NATIONAL DES SCIENCES APPLIQUEES DE ROUEN (INSA), Saint Etienne Du Rouvray (FR)

( * ) Notice: Subject to any disclaimer, the term of this patent is extended or adjusted under 35 U.S.C. 154(b) by 0 days.

(21) Appl. No.: 14/432,269

(22) PCT Filed: Oct. 1, 2013

(86) PCT No.: PCT/EP2013/070488
§ 371 (c)(1),
(2) Date: Mar. 30, 2015

(87) PCT Pub. No.: WO2014/053516
PCT Pub. Date: Apr. 10, 2014

(65) Prior Publication Data
US 2015/0336907 A1   Nov. 26, 2015

(30) Foreign Application Priority Data
Oct. 1, 2012   (EP) .................. 12306196

(51) Int. Cl.
C07D 253/07    (2006.01)
C07D 401/12    (2006.01)
A61K 31/53     (2006.01)
A61P 31/12     (2006.01)
C07D 253/075   (2006.01)

(52) U.S. Cl.
CPC .......... *C07D 253/075* (2013.01); *C07D 253/07* (2013.01); *C07D 401/12* (2013.01)

(58) Field of Classification Search
CPC .......................... C07D 253/07; A61K 31/53
USPC .......................................... 544/182; 514/242
See application file for complete search history.

(56) References Cited

U.S. PATENT DOCUMENTS 6,329,381 B1   12/2001   Kurimoto et al.

FOREIGN PATENT DOCUMENTS

| EP | 0882727 A1 | 12/1998 |
|----|------------|---------|
| WO | 98/01448 A1 | 1/1998 |
| WO | 99/28321 A1 | 6/1999 |
| WO | 2006/015985 A1 | 2/2006 |
| WO | 2006/117670 A1 | 11/2006 |
| WO | 2009/067081 A1 | 5/2009 |
| WO | 2012/067269 A1 | 5/2012 |

OTHER PUBLICATIONS

Vippagunta et al., Advanced Drug Delivery Reviews 48: 3-26, 2001.*
Ulrich J. Kirk-Othmer Encyclopedia of Chemical Technology, John Wiley & Sons, Inc, pp. 1-7, 2002.*
Ohto et al., Microbes and Infection 16 (2014) 273-282.*
Yu et al. Biochimica et Biophysica Acta 1835(2013)144-154.*
Cecil Textbook of Medicine, edited by Bennet, J.C., and Plum F., 20th edition, vol. 1, 1004-101 0, 1996.*
Freshney et al., Culture of Animal Cells, a Manual of Basic Technique, Alan R. Liss, Inc., 1983, New York, p. 4.*
Dermer et al., Bio/Technology, 1994, 12:320.*
Zhao et al., Frontiers in Immunology. 5, 1-6,2014.*
Hoffman: "The immune response of *Drosophila*," Nature, vol. 426, pp. 33-38, Nov. 6, 2003.
Takeda et al.: "Toll-Like Receptors," Annual Rev. Immunology, vol. 21, pp. 335-376, Jan. 9, 2003.
Ulevitch: "Therapeutics Targeting the Innate Immune System," Nature Reviews, Immunology, vol. 4, pp. 512-520, Jul. 2004.

* cited by examiner

*Primary Examiner* — Venkataraman Balasubramanian
(74) *Attorney, Agent, or Firm* — Buchanan Ingersoll & Rooney PC

(57) ABSTRACT

This invention relates to 1,2,4-triazine derivatives, processes for their preparation, pharmaceutical compositions, and their use in treating viral infections.

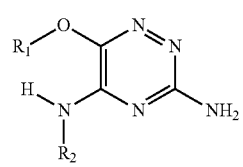

7 Claims, No Drawings

SEQUENCE LISTING

<160> NUMBER OF SEQ ID NOS: 1

<210> SEQ ID NO 1
<211> LENGTH: 12
<212> TYPE: DNA
<213> ORGANISM: Artificial Sequence
<220> FEATURE:
<223> OTHER INFORMATION: ISRE element

```
<400> SEQUENCE: 1
gaaactgaaa ct                                                  12
```

1,2,4-TRIAZINE DERIVATIVES FOR THE TREATMENT OF VIRAL INFECTIONS

CROSS-REFERENCE TO RELATED APPLICATIONS

This application is a U.S. National Stage Application pursuant to 35 U.S.C. §371 of International Patent Application PCT/EP2013/070488, filed on Oct. 1, 2013, and published as WO 2014/053516 on Apr. 10, 2014, which claims priority to European Patent Application 12306196.2, filed on Oct. 1, 2012, all of which are incorporated herein by reference in their entireties for all purposes.

This invention relates to 1,2,4-triazine derivatives, processes for their preparation, pharmaceutical compositions, and their use in treating viral infections.

The present invention relates to the use of 1,2,4-triazine derivatives in the treatment of viral infections, immune or inflammatory disorders, whereby the modulation, or agonism, of toll-like-receptors (TLRs) is involved. Toll-Like Receptors are primary transmembrane proteins characterized by an extracellular leucine rich domain and a cytoplasmic extension that contains a conserved region. The innate immune system can recognize pathogen-associated molecular patterns via these TLRs expressed on the cell surface of certain types of immune cells. Recognition of foreign pathogens activates the production of cytokines and upregulation of co-stimulatory molecules on phagocytes. This leads to the modulation of T cell behaviour.

It has been estimated that most mammalian species have between ten and fifteen types of Toll-like receptors. Thirteen TLRs (named TLR1 to TLR13) have been identified in humans and mice together, and equivalent forms of many of these have been found in other mammalian species. However, equivalents of certain TLR found in humans are not present in all mammals. For example, a gene coding for a protein analogous to TLR10 in humans is present in mice, but appears to have been damaged at some point in the past by a retrovirus. On the other hand, mice express TLRs 11, 12, and 13, none of which are represented in humans. Other mammals may express TLRs which are not found in humans. Other non-mammalian species may have TLRs distinct from mammals, as demonstrated by TLR14, which is found in the *Takifugu pufferfish*. This may complicate the process of using experimental animals as models of human innate immunity.

For reviews on TLRs see the following journal articles. Hoffmann, J. A., Nature, 426, p 33-38, 2003; Akira, S., Takeda, K., and Kaisho, T., Annual Rev. Immunology, 21, p 335-376, 2003; Ulevitch, R. J., Nature Reviews: Immunology, 4, p 512-520, 2004.

Compounds indicating activity on Toll-Like receptors have been previously described such as purine derivatives in WO 2006/117670, adenine derivatives in WO 98/01448 and WO 99/28321, and pyrimidines in WO 2009/067081.

However, there exists a strong need for novel Toll-Like receptor modulators having preferred selectivity, higher potency, higher metabolic stability, and an improved safety profile compared to the compounds of the prior art.

In accordance with the present invention a compound of formula (I) is provided

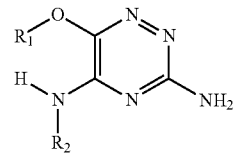

or a pharmaceutically acceptable salt, tautomer(s), solvate or polymorph thereof, wherein $R_1$ is $C_{1-6}$ alkyl, arylalkyl, or heteroarylalkyl each of which is optionally substituted by one or more substituents independently selected from halogen, hydroxyl, amino, $C_{1-6}$ alkyl, di-$(C_{1-6})$alkylamino, $C_{1-6}$ alkylamino, $C_{1-6}$ alkoxy, $C_{3-6}$ cycloalkyl, carboxylic acid, carboxylic ester, carboxylic amide, heterocycle, aryl, alkenyl, alkynyl, arylalkyl, heteroaryl, heteroarylalkyl, or nitrile.

$R_2$ is $C_{1-8}$ alkyl, optionally substituted by one or more substituents independently selected from halogen, hydroxyl, amino, $C_{1-3}$ alkyl, $C_{1-3}$ alkoxy, $C_{3-6}$ cycloalkyl, carboxylic acid, carboxylic ester, carboxylic amide, di-$(C_{1-6})$alkylamino, $C_{1-6}$ alkylamino, aryl, heteroaryl, heteroarylalkyl or nitrile.

In a first embodiment the present invention provides compounds of formula (I) wherein $R_2$ is butyl or pentyl and wherein $R_1$ is as specified above.

In a further embodiment the invention concerns compounds of formula (I) wherein $R_2$ is $C_{1-8}$ alkyl substituted with hydroxyl, and wherein $R_1$ is a substituted or unsubstituted arylalkyl group.

In a further embodiment the current invention relates to compounds of formula (I) wherein $R_1$ is an arylalkyl and $R_2$ is $C_{1-8}$ alkyl substituted with a hydroxyl, or one of the following examples in any stereochemical configuration:

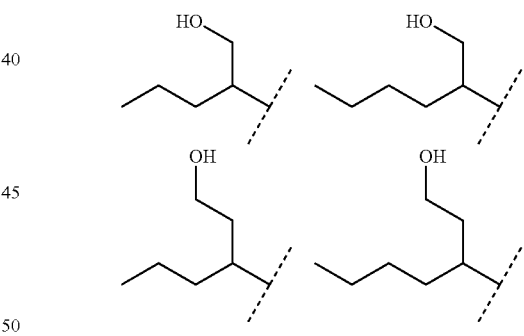

Furthermore the present invention also provides compounds of formula (I) wherein $R_1$ is $CH_3$ and wherein $R_2$ is as specified above.

In another embodiment the present invention provides compounds of formula (I) wherein $R_1$ is a heteroarylalkyl, and wherein $R_2$ is as specified above.

The compounds of formula (I) and their pharmaceutically acceptable salt, tautomer(s), solvate or polymorph thereof have activity as pharmaceuticals, in particular as modulators of Toll-Like Receptors (especially TLR7 and/or TLR8) activity.

In a further aspect the present invention provides a pharmaceutical composition comprising a compound of formula (I) or a pharmaceutically acceptable salt, solvate or polymorph thereof together with one or more pharmaceutically acceptable excipients, diluents or carriers.

Furthermore a compound of formula (I) or a pharmaceutically acceptable salt, solvate or polymorph thereof according to the current invention, or a pharmaceutical composition comprising said compound of formula (I) or a pharmaceutically acceptable salt, solvate or polymorph thereof can be used as a medicament.

Another aspect of the invention is that a compound of formula (I) or a pharmaceutically acceptable salt, solvate or polymorph thereof, or said pharmaceutical composition comprising said compound of formula (I) or a pharmaceutically acceptable salt, solvate or polymorph thereof can be used accordingly in the treatment of a disorder in which the modulation of TLR7 and/or TLR8 is involved.

The term "alkyl" refers to a straight-chain or branched-chain saturated aliphatic hydrocarbon containing the specified number of carbon atoms.

The term "halogen" refers to fluorine, chlorine, bromine or iodine.

The term "alkenyl" refers to an alkyl as defined above consisting of at least two carbon atoms and at least one carbon-carbon double bond.

The term "alkynyl" refers to an alkyl as defined above consisting of at least two carbon atoms and at least one carbon-carbon triple bond.

The term "cycloalkyl" refers to a carbocyclic ring containing the specified number of carbon atoms.

The term "aryl" means an aromatic ring structure optionally comprising one or two heteroatoms selected from N, O and S, in particular from N and O. Said aromatic ring structure may have 4, 5, 6 or 7 ring atoms. In particular, said aromatic ring structure may have 5 or 6 ring atoms.

The term "heteroaryl" means an aromatic ring structure as defined for the term "aryl" comprising at least 1 heteroatom selected from N, O and S, in particular from N and O.

The term "bicyclic heterocycle" means an aromatic ring structure, as defined for the term "aryl" comprised of two fused aromatic rings. Each ring is optionally comprised of heteroatoms selected from N, O and S, in particular from N and O The term "arylalkyl" means an aromatic ring structure as defined for the term "aryl" optionally substituted with an alkyl group.

The term "heteroarylalkyl" means an aromatic ring structure as defined for the term "heteroaryl" optionally substituted by an alkyl group.

The term "alkoxy" refers to an alkyl (carbon and hydrogen chain) group singular bonded to oxygen like for instance a methoxy group or ethoxy group.

"Heterocycle" refers to molecules that are saturated or partially saturated and include ethyloxide, tetrahydrofuran, dioxane or other cyclic ethers. Heterocycles containing nitrogen include, for example azetidine, morpholine, piperidine, piperazine, pyrrolidine, and the like. Other heterocycles include, for example, thiomorpholine, dioxolinyl, and cyclic sulfones.

"Heteroaryl" groups are heterocyclic groups which are aromatic in nature. These are monocyclic, bicyclic, or polycyclic containing one or more heteroatoms selected from N, O or S. Heteroaryl groups can be, for example, imidazolyl, isoxazolyl, furyl, oxazolyl, pyrrolyl, pyridonyl, pyridyl, pyridazinyl, or pyrazinyl.

Pharmaceutically acceptable salts of the compounds of formula (I) include the acid addition and base salts thereof. Suitable acid addition salts are formed from acids which form non-toxic salts. Suitable base salts are formed from bases which form non-toxic salts.

The compounds of the invention may also exist in unsolvated and solvated forms. The term "solvate" is used herein to describe a molecular complex comprising the compound of the invention and one or more pharmaceutically acceptable solvent molecules, for example, ethanol.

The term "polymorph" refers to the ability of the compound of the invention to exist in more than one form or crystal structure.

The compounds of the present invention may be administered as crystalline or amorphous products. They may be obtained for example as solid plugs, powders, or films by methods such as precipitation, crystallization, freeze drying, spray drying, or evaporative drying. They may be administered alone or in combination with one or more other compounds of the invention or in combination with one or more other drugs. Generally, they will be administered as a formulation in association with one or more pharmaceutically acceptable excipients. The term "excipient" is used herein to describe any ingredient other than the compound(s) of the invention. The choice of excipient depends largely on factors such as the particular mode of administration, the effect of the excipient on solubility and stability, and the nature of the dosage form.

The compounds of the present invention or any subgroup thereof may be formulated into various pharmaceutical forms for administration purposes. As appropriate compositions there may be cited all compositions usually employed for systemically administering drugs. To prepare the pharmaceutical compositions of this invention, an effective amount of the particular compound, optionally in addition salt form, as the active ingredient is combined in intimate admixture with a pharmaceutically acceptable carrier, which carrier may take a wide variety of forms depending on the form of preparation desired for administration. These pharmaceutical compositions are desirably in unitary dosage form suitable, for example, for oral, rectal, or percutaneous administration. For example, in preparing the compositions in oral dosage form, any of the usual pharmaceutical media may be employed such as, for example, water, glycols, oils, alcohols and the like in the case of oral liquid preparations such as suspensions, syrups, elixirs, emulsions, and solutions; or solid carriers such as starches, sugars, kaolin, diluents, lubricants, binders, disintegrating agents and the like in the case of powders, pills, capsules, and tablets. Because of their ease in administration, tablets and capsules represent the most advantageous oral dosage unit forms, in which case solid pharmaceutical carriers are obviously employed. Also included are solid form preparations that can be converted, shortly before use, to liquid forms. In the compositions suitable for percutaneous administration, the carrier optionally comprises a penetration enhancing agent and/or a suitable wetting agent, optionally combined with suitable additives of any nature in minor proportions, which additives do not introduce a significant deleterious effect on the skin. Said additives may facilitate the administration to the skin and/or may be helpful for preparing the desired compositions. These compositions may be administered in various ways, e.g., as a transdermal patch, as a spot-on, as an ointment. The compounds of the present invention may also be administered via inhalation or insufflation by means of methods and formulations employed in the art for administration via this way. Thus, in general the compounds of the present invention may be administered to the lungs in the form of a solution, a suspension or a dry powder.

It is especially advantageous to formulate the aforementioned pharmaceutical compositions in unit dosage form for ease of administration and uniformity of dosage. Unit dosage form as used herein refers to physically discrete units suitable as unitary dosages, each unit containing a predetermined quantity of active ingredient calculated to produce the desired therapeutic effect in association with the required pharmaceutical carrier. Examples of such unit dosage forms are tablets (including scored or coated tablets), capsules, pills, powder packets, wafers, suppositories, injectable solutions or suspensions and the like, and segregated multiples thereof.

Those of skill in the treatment of infectious diseases will be able to determine the effective amount from the test results presented hereinafter. In general it is contemplated that an effective daily amount would be from 0.01 mg/kg to 50 mg/kg body weight, more preferably from 0.1 mg/kg to 10 mg/kg body weight. It may be appropriate to administer the required dose as two, three, four or more sub-doses at appropriate intervals throughout the day. Said sub-doses may be formulated as unit dosage forms, for example, containing 1 to 1000 mg, and in particular 5 to 200 mg of active ingredient per unit dosage form.

The exact dosage and frequency of administration depends on the particular compound of formula (I) used, the particular condition being treated, the severity of the condition being treated, the age, weight and general physical condition of the particular patient as well as other medication the individual may be taking, as is well known to those skilled in the art. Furthermore, it is evident that the effective amount may be lowered or increased depending on the response of the treated subject and/or depending on the evaluation of the physician prescribing the compounds of the instant invention. The effective amount ranges mentioned above are therefore only guidelines and are not intended to limit the scope or use of the invention to any extent.

Preparation of compounds of formula (I)

EXPERIMENTAL SECTION

Preparation of 2

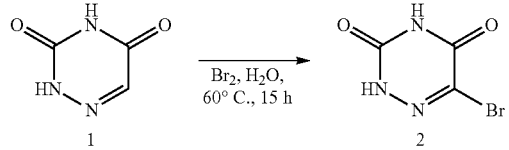 [SMILES: O=c1cn[nH]c(=O)[nH]1 ; O=c1[nH]nc(Br)c(=O)[nH]1]

To a solution of 1 (20 g, 176.9 mmol, 1 eq.) in $H_2O$ (320 mL) was added $Br_2$ (24 mL, 466.8 mmol, 2.6 eq.) at room temperature. The mixture was stirred at 60° C. for 15 hours followed by addition of $NH_4OH$ (50 mL) at room temperature. HCl (6N aq.) was then added slowly until pH=5 and the mixture was extracted with ethyl acetate (3×800 mL). The combined organic layers were washed with water and brine, dried ($MgSO_4$), the solids were removed by filtration, and the solvents of the filtrate were concentrated under reduced pressure to obtain 2 (16 g).

$^1$H NMR (400 MHz, DMSO-$d_6$) □ ppm 12.56 (m, 1H), 12.31 (m, 1H)

Preparation of 3

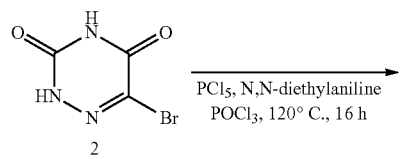

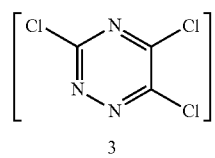

To a solution of 2 (16 g, 83.3 mmol) in $POCl_3$ (80 mL) were added $PCl_5$ (36.1 g, 173.4 mmol) and N,N-diethylaniline (35 mL, 221.7 mmol) at room temperature. The mixture was stirred at 120° C. for 5 hours then the excess solvent was removed under reduced pressure. The residue, 3 (80 g), was used directly in the next step without further purification.

Preparation of 4

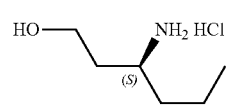

Intermediate 4 was synthesized according to the preparation of 9, employing butyraldehyde in place of valeraldehyde.

$^1$H NMR (400 MHz, DMSO-$d_6$): □ ppm 8.07 (s, 3H), 4.85 (br, 1H), 3.57-3.45 (m, 2H), 3.14-3.12 (m, 1H), 1.70-1.64 (m, 2H), 1.56-1.49 (m, 2H), 1.38-1.30 (m, 2H), 0.90-0.80 (t, J=6.8 Hz, 3H).

Preparation of 5

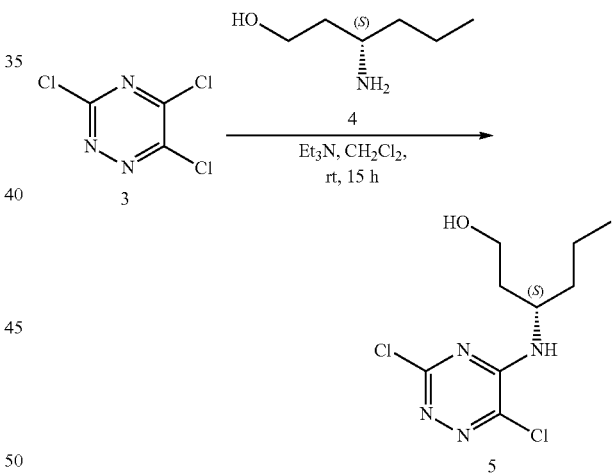

To a stirred solution of 3 (80 g crude, 82.8 mmol) in $CH_2Cl_2$ (300 mL) was added 4 (12.8 g, 82.8 mmol) and $Et_3N$ (34.7 mL, 250 mmol) at room temperature. The mixture was stirred 15 hours at room temperature. The reaction was diluted with water (400 mL) and extracted with $CH_2Cl_2$ (3×500 mL). The combined organic layers were washed with water and brine, then dried ($MgSO_4$), the solids were removed by filtration, and the solvents of the filtrate were removed under reduced pressure. The residue was purified by column chromatography over silica gel using a petroleum ether to ethyl acetate gradient. The best fractions were pooled and the solvents were removed under reduced pressure to afford 5 (3 g).

$^1$H NMR (400 MHz, $CDCl_3$): □ ppm 6.85 (d, 1H), 4.35 (m, 1H), 3.83 (m, 2H), 2.0 (m, 1H), 1.71 (m, 3H), 1.38 (m, 2H), 0.98 (t, 3H).

Preparation of 6

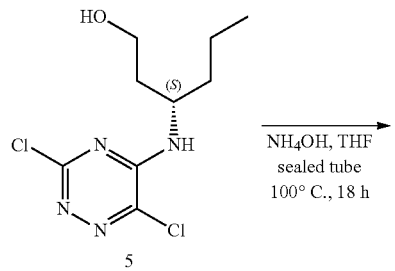

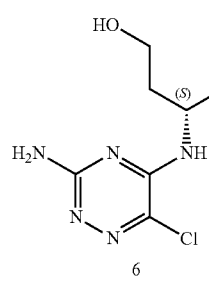

5 (3 g, 11.32 mmol, 1 eq.) and NH₄OH (20 mL) in THF (20 mL) were placed in a sealed tube and heated to 100° C. for 18 hours. After cooling to room temperature, the reaction was diluted with water and extracted with ethyl acetate (3×50 mL). The combined organic layers were washed with brine, dried (MgSO₄), the solids were removed by filtration and the solvents of the filtrate were concentrated under reduced pressure. The residue was purified by silica gel column chromatography using a CH₂Cl₂ to CH₂Cl₂/CH₃OH gradient. The best fractions were pooled and the solvents of the filtrate were removed under reduced pressure to afford 6 (1.57 g).

¹H NMR (400 MHz, CDCl₃): $\square$ ppm 5.65 (d, 1H), 5.20 (brs, 2H), 4.35 (m, 1H), 3.65 (m, 2H), 2.0 (m, 1H), 1.60 (m, 3H), 1.45 (m, 2H), 0.93 (t, 3H).

Preparation of 8

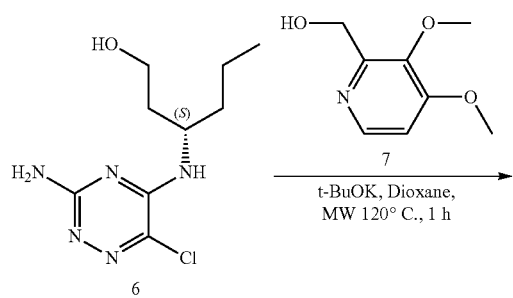

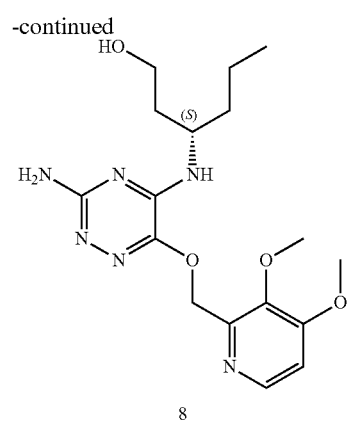

A mixture of 6 (1.2 g, 4.9 mmol), 7 (4.13 g, 24.4 mmol) and t-BuOK (1.6 g, 14.7 mmol) in dioxane (48 mL) was stirred at 120° C. in the microwave for 1 hour. The solution solids were removed by filtration and the filtrate was concentrated under reduced pressure. The residue was purified by preparative high-performance liquid chromatography (C18 column, using a water (containing 0.05% aq. NH₃ as a modifier) to acetonitrile gradient. The desired fractions were pooled and the solvents were removed under reduced pressure to afford 8 (100 mg).

¹H NMR (400 MHz, methanol-d₄): $\square$ ppm 8.56 (d, 1H), 7.73 (d, 1H), 5.69 (s, 2H), 4.54 (m, 1H), 4.25 (s, 3H), 4.06 (s, 3H), 3.65 (m, 2H), 1.75 (m, 4H), 1.35 (m, 2H), 0.94 (t, 3H).

Overall Preparation of 9

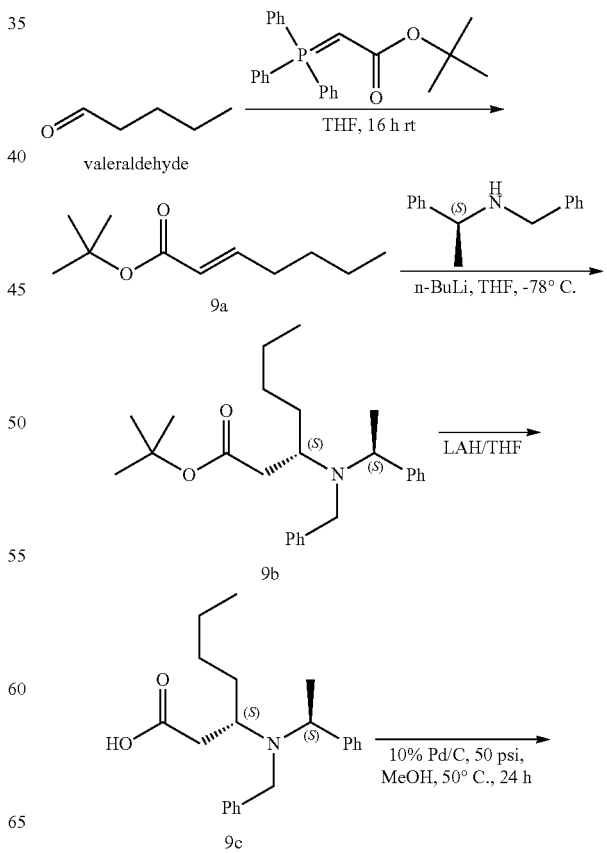

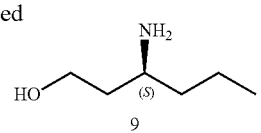

Preparation of Intermediate 9a

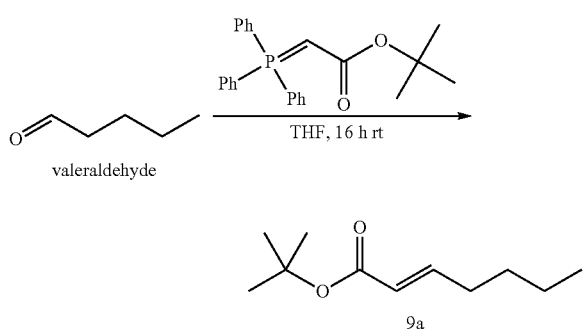

To a solution of valeraldehyde (43 g, 500 mmol) in THF (1 L) was added (tert-butoxycarbonylmethylene)triphenylphosphorane (200 g, 532 mmol) and the reaction mixture was stirred for 16 hours at room temperature. The solvent was removed under reduced pressure and the residue was diluted in petroleum ether and filtered. The solvents of the filtrate were removed under reduced pressure and the residue was purified by silica chromatography using a petroleum ether to 3% ethyl acetate in petroleum ether gradient to give 9a (90 g) as a colorless oil.

$^1$H NMR (400 MHz, CDCl$_3$): ☐ ppm 6.81-6.77 (m, 1H), 5.68-5.64 (td, J=1.2 Hz, 15.6 Hz, 1H), 2.11-2.09 (m, 2H), 1.406 (s, 9H), 1.38-1.26 (m, 4H), 0.85-0.81 (t, J=7.2 Hz, 3H).

Preparation of compound 9b

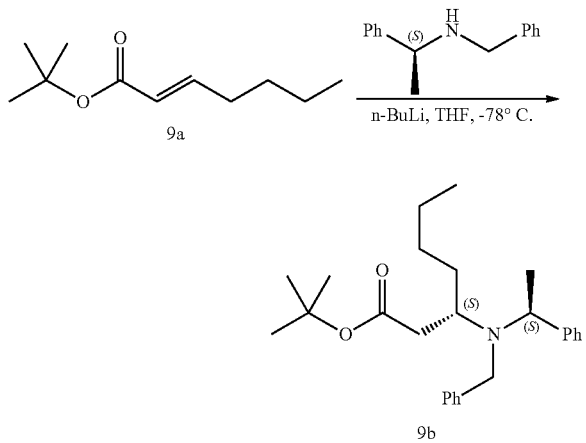

n-butyl lithium (290 mL, 725 mmol) was added to a stirred solution of (S)-(−)-N-benzyl-1-phenylethylamine (165 g, 781 mmol) in THF (800 mL) at −78° C. The reaction mixture was stirred for 30 minutes then 9a (90 g, 488.4 mmol) in THF (400 mL) was added and the reaction was stirred for 2 hours at −78° C. The mixture was quenched with sat., aq. NH$_4$Cl solution and warmed to room temperature. The product was partitioned between ethyl acetate and water. The organic phase was washed with brine, dried over magnesium sulfate, the solids were removed by filtration, and the solvents of the filtrate were removed under reduced pressure. The residue was purified by column chromatography eluting with 5% ethyl acetate in petroleum ether to afford a colorless oil, 9b (132 g).

$^1$H NMR (400 MHz, CDCl$_3$): ☐ ppm 7.36-7.16 (m, 10H), 3.75-3.70 (m, 2H), 3.43-3.39 (d, J=15.2 Hz, 1H), 3.33-3.15 (m, 1H), 1.86-1.80 (m, 2H), 1.47-1.37 (m, 2H), 1.32 (s, 9H), 1.26-1.17 (m, 7H), 0.83-0.79 (t, J=7.2 Hz, 3H).

Preparation of 9c

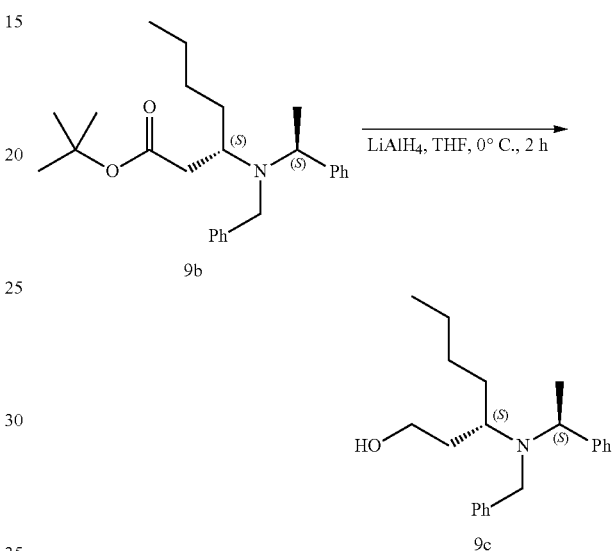

9b (130 g, 328 mmol) was dissolved in THF (1.5 L) and LiAlH$_4$ (20 g, 526 mmol) was added at 0° C. in small portions. The resulting mixture was stirred at the same temperature for 2 hours and then allowed to warm to room temperature. The mixture was quenched with a sat. aq. NH$_4$Cl solution. The product was partitioned between ethyl acetate and water. The organic phase was washed with brine, dried and evaporated. The combined organic layers were dried over sodium sulfate, the solids were removed via filtration and concentrated to afford crude 9c (100 g), which was used in the next step without further purification.

$^1$H NMR (400 MHz, CDCl$_3$): ☐ ppm 7.33-7.14 (m, 10H), 3.91-3.86 (m, 1H), 3.80-3.77 (d, J=13.6 Hz, 1H), 3.63-3.60 (d, J=13.6 Hz, 1H), 3.43-3.42 (m, 1H), 3.15-3.10 (m, 1H), 2.70-2.63 (m, 2H), 1.65-1.28 (m, 10H), 0.89-0.81 (m, 3H).

Preparation of 9

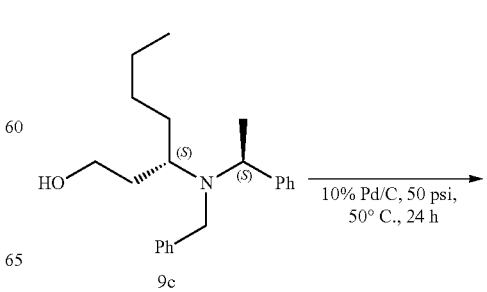

Preparation of 11

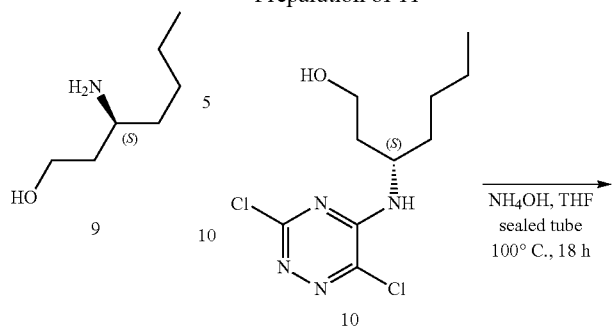

A solution of 9c (38 g, 116.75 mmol) and 10% Pd/C in methanol (200 mL) was hydrogenated under 50 psi hydrogen at 50° C. for 24 hours. The reaction mixture was filtered and the solvent was evaporated to give 9.

$^1$H NMR (400 MHz, DMSO-$d_6$): □ ppm 8.04 (s, 3H), 3.60-3.49 (m, 2H), 3.16-3.15 (m, 1H), 1.71-1.67 (m, 2H), 1.60-1.55 (m, 2H), 1.33-1.26 (m, 4H), 0.90-0.87 (t, J=6.8 Hz, 3H).

Preparation of 10

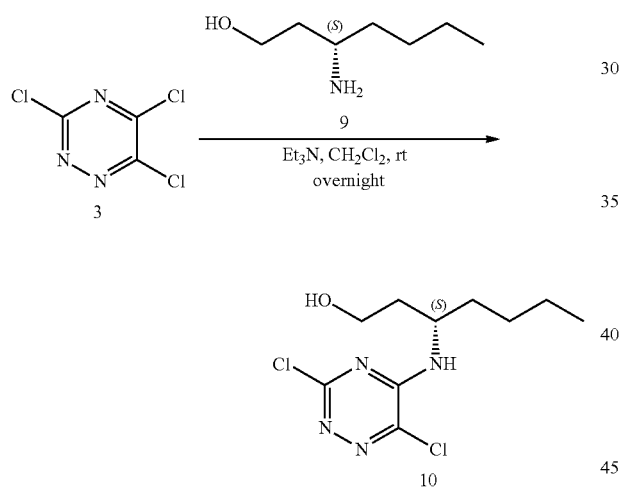

To a stirred solution of 3 (21.6 g crude, 22.1 mmol) in CH$_2$Cl$_2$ (54 mL) was added 9 (2.9 g, 22.1 mmol) and Et$_3$N (9.2 ml, 66.3 mmol) at room temperature. The mixture was then stirred during the night at the same temperature. The reaction was diluted with water (200 mL) and extracted with CH$_2$Cl$_2$ (3×150 mL). The combined organic layers were washed with water and brine, dried (MgSO$_4$), the solids were removed via filtration, and the solvents of the filtrate were concentrated under reduced pressure. The crude was purified by silica gel column chromatography using a petroleum ether to ethyl acetate gradient. The best fractions were pooled, and the solvents were removed under reduced pressure to afford 10 (0.91 g).

$^1$H NMR (400 MHz, CDCl$_3$) □ ppm 6.71 (d, 1H), 4.36 (m, 1H), 3.83 (m, 2H), 2.04 (m, 2H), 1.70 (m, 2H), 1.35 (m, 4H), 0.92 (t, 3H)

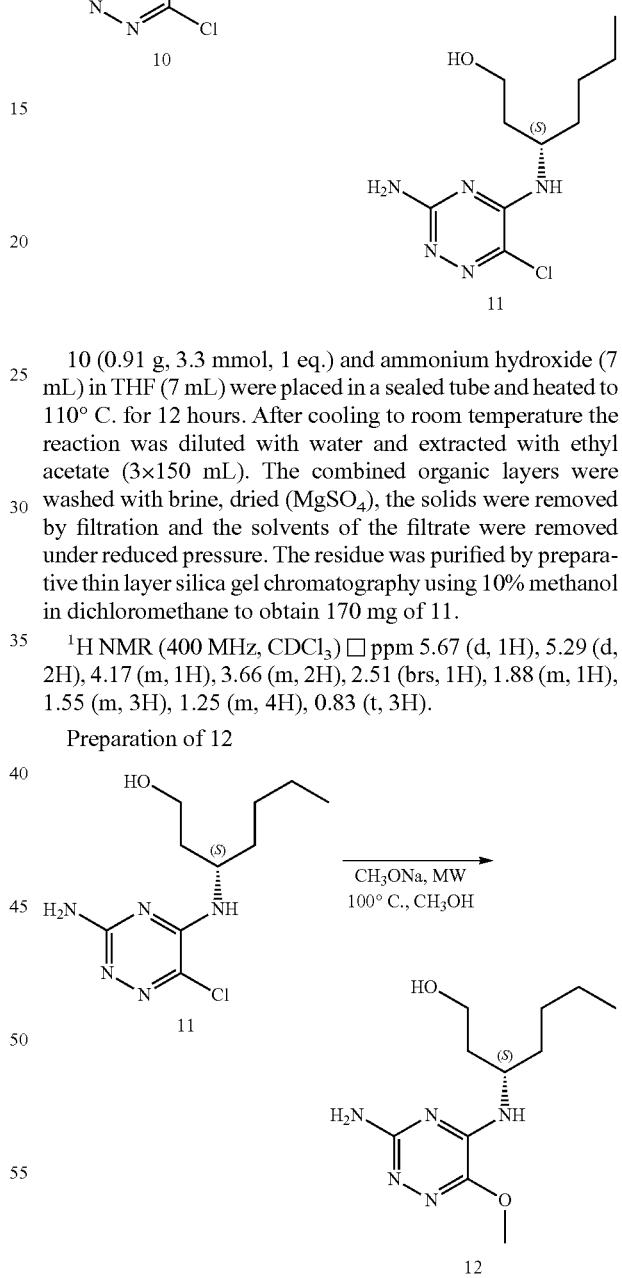

10 (0.91 g, 3.3 mmol, 1 eq.) and ammonium hydroxide (7 mL) in THF (7 mL) were placed in a sealed tube and heated to 110° C. for 12 hours. After cooling to room temperature the reaction was diluted with water and extracted with ethyl acetate (3×150 mL). The combined organic layers were washed with brine, dried (MgSO$_4$), the solids were removed by filtration and the solvents of the filtrate were removed under reduced pressure. The residue was purified by preparative thin layer silica gel chromatography using 10% methanol in dichloromethane to obtain 170 mg of 11.

$^1$H NMR (400 MHz, CDCl$_3$) □ ppm 5.67 (d, 1H), 5.29 (d, 2H), 4.17 (m, 1H), 3.66 (m, 2H), 2.51 (brs, 1H), 1.88 (m, 1H), 1.55 (m, 3H), 1.25 (m, 4H), 0.83 (t, 3H).

Preparation of 12

A mixture of 11 (170 mg, 0.64 mmol) and sodium methoxide (69 mg, 1.28 mmol) in CH$_3$OH (10 mL) was heated to 100° C. in the microwave with stirring for 1 hour. The solids were removed by filtration and the filtrate was concentrated under reduced pressure. The residue was purified by preparative high-performance liquid chromatography (column C18, using a water to acetonitrile gradient containing 0.05% HCl).

The best fractions were pooled and concentrated under vacuum to afford 12.

LC-MS m/z=256 (M+H)

$^1$H NMR (400 MHz, MeOH-d$_4$) ☐ ppm 4.49 (m, 1H), 4.02 (s, 3H), 3.63 (m, 2H), 1.84 (m, 2H), 1.68 (m, 2H), 1.33 (m, 4H), 0.93 (t, 3H).

Preparation of 13

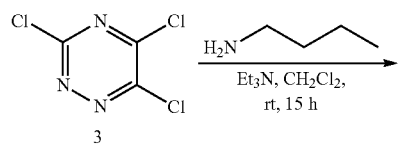

Intermediate 13 was prepared according to the method to prepare 5.

Preparation of 14

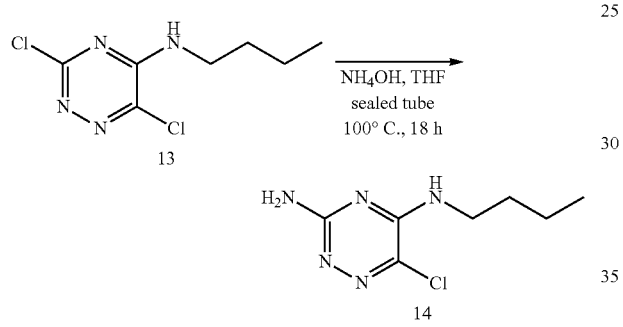

Intermediate 14 was prepared according to the method to prepare 6.

Preparation of 15

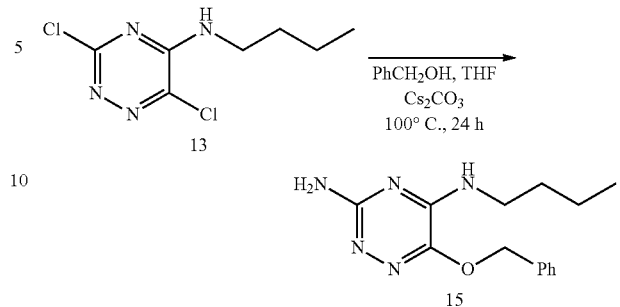

In a sealed tube, a mixture of 14 (100 mg, 0.5 mmol), benzylalcohol (0.52 mL, 5 mmol) and cesium carbonate (814.5 mg, 2.5 mmol) in anhydrous THF (1 mL) was stirred at 100° C. for 24 hours. The reaction was diluted with water (1 mL) and extracted with ethyl acetate (3×10 mL). The combined organic extracts were washed with water and brine, dried (MgSO4), the solids were removed by filtration, and the solvents of the filtrate were removed under reduced pressure. The crude was purified by silica gel chromatography using a petroleum ether to ethyl acetate gradient affording a yellow oil, 15 (67.7 mg, 0.25 mmol).

Preparation of 16

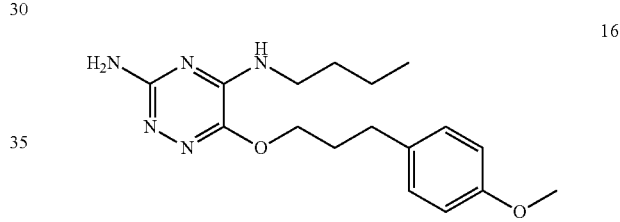

16 was prepared according to the method to prepare 15.

TABLE I

Compounds of formula (I). The following compounds were synthesized according to one of the methods described above.

| # | STRUCTURE | H NMR | LC Method, Retention Time (min) | Mass Found (M + H) |
|---|---|---|---|---|
| 8 | 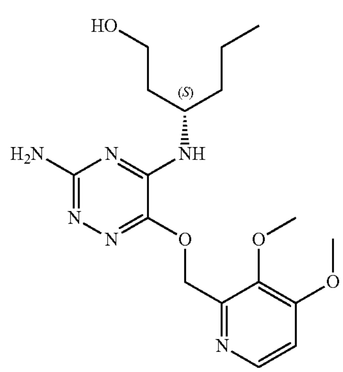 | $^1$H NMR (400 MHz, methanol-d$_4$) δ ppm 8.56 (d, 1 H), 7.73 (d, 1 H), 5.69 (s, 2 H), 4.54 (m, 1 H), 4.25 (s, 3 H), 4.06 (s, 3 H), 3.65 (m, 2 H), 1.75 (m, 4 H), 1.35 (m, 2 H), 0.94 (t, 3H) exchangeable protons not seen. | A, 3.30 | 379 |

TABLE I-continued

Compounds of formula (I). The following compounds were synthesized according to one of the methods described above.

| # | STRUCTURE | H NMR | LC Method, Retention Time (min) | Mass Found (M + H) |
|---|---|---|---|---|
| 12 | 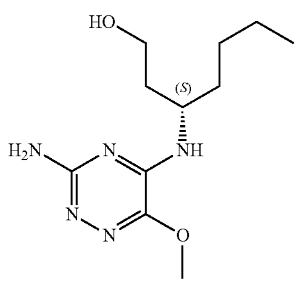 | $^1$H NMR (400 MHz, MeOH-$d_4$) δ ppm 4.49 (m, 1 H), 4.02 (s, 3 H), 3.63 (m, 2 H), 1.84 (m, 2 H), 1.68 (m, 2 H), 1.33 (m, 4 H), 0.93 (t, 3H) exchangeable protons not seen. | A, 3.55 | 256 |
| 15 | 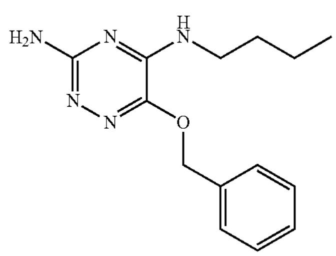 [SMILES: CCCCNc1nc(N)nnc1OCc1ccccc1] | $^1$H NMR (500 MHz, DMSO-$d_6$) δ 7.48 (d, J = 7.25 Hz, 2H), 7.35-7.42 (m, 3H), 7.27-7.34 (m, 1H), 5.71 (s, 2H), 5.32 (s, 2H), 3.23-3.35 (m, 2H), 1.51 (quin, J = 7.25 Hz, 2H), 1.20-1.33 (m, 2H), 0.88 (t, J = 7.25 Hz, 3H) | B, 2.61 | 274 |
| 16 | 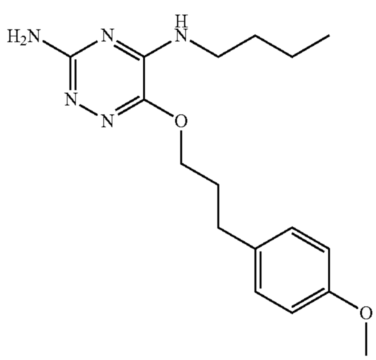 [SMILES: CCCCNc1nc(N)nnc1OCCCc1ccc(OC)cc1] | $^1$H NMR (500 MHz, DMSO-$d_6$) δ 7.25 (t, J = 5.67 Hz, 1H), 7.14 (d, J = 8.51 Hz, 2H), 6.84 (d, J = 8.51 Hz, 2H), 5.66 (s, 2H), 4.16 (t, J = 6.46 Hz, 2H), 3.71 (s, 3H), 3.26-3.35 (m, 2H), 2.69 (t, J = 7.57 Hz, 2H), 1.95-2.03 (m, 2H), 1.48-1.56 (m, 2H), 1.25-1.33 (m, 2H), 0.89 (t, J = 7.41 Hz, 3H) | B, 2.79 | 332 |
| 17 | 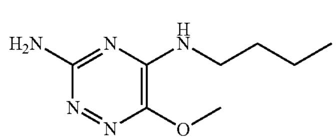 | $^1$H NMR (400 MHz, METHANOL-$d_4$) δ ppm 0.96 (t, J = 7.4 Hz, 3 H), 1.33-1.45 (m, 2 H), 1.57-1.71 (m, 2 H), 3.53 (t, J = 7.3 Hz, 2 H), 3.99 (s, 3 H), exchangeable protons not seen. | A, 3.26 | 198 |
| 18 | 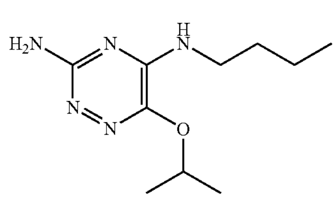 [SMILES: CCCCNc1nc(N)nnc1OC(C)C] | $^1$H NMR (400 MHz, METHANOL-$d_4$) δ ppm 0.99 (t, J = 7.4 Hz, 3 H), 1.35-1.44 (m, 2 H), 1.44 (d, J = 1.0 Hz, 6 H), 1.59-1.75 (m, 2 H), 3.55 (t, J = 7.4 Hz, 2 H), 5.07-5.22 (m, 1 H), exchangeable protons not seen. | A, 3.94 | 226 |

TABLE I-continued

Compounds of formula (I). The following compounds were synthesized according to one of the methods described above.

| # | STRUCTURE | H NMR | LC Method, Retention Time (min) | Mass Found (M + H) |
|---|---|---|---|---|
| 19 | 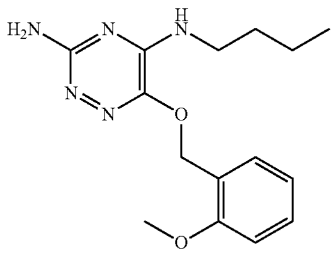 [SMILES: CCCCNc1nc(N)nnc1OCc1ccccc1OC] | $^1$H NMR (400 MHz, CHLOROFORM-d) δ ppm 0.86 (t, J = 7.3 Hz, 3 H), 1.23-1.36 (m, 2 H), 1.44-1.56 (m, 2 H), 3.27-3.37 (m, 2 H), 3.77 (s, 3 H), 4.44 (br. s., 2 H), 5.36 (s, 2 H), 5.47 (br. s., 1 H), 6.81-6.93 (m, 2 H), 7.27 (td, J = 7.9, 1.8 Hz, 1 H), 7.32 (dd, J = 7.3, 1.5 Hz, 1 H) | C, 3.38 | 304 |
| 20 | 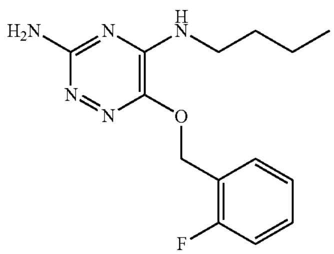 [SMILES: CCCCNc1nc(N)nnc1OCc1ccccc1F] | $^1$H NMR (400 MHz, METHANOL-d$_4$) δ ppm 0.97 (t, J = 7.4 Hz, 3 H), 1.32-1.45 (m, 2 H), 1.58-1.69 (m, 2 H), 3.53 (t, J = 7.3 Hz, 2 H), 5.45 (s, 2 H), 7.13-7.21 (m, 1 H), 7.25 (td, J = 7.5, 1.0 Hz, 1 H), 7.41-7.49 (m, 1 H), 7.61 (td, J = 7.5, 1.8 Hz, 1 H) exchangeable protons not seen. | C, 3.36 | 292 |
| 21 | 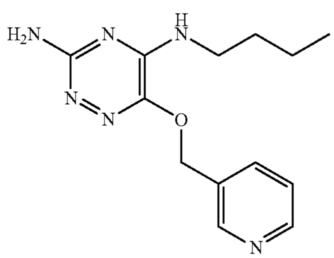 [SMILES: CCCCNc1nc(N)nnc1OCc1cccnc1] | $^1$H NMR (400 MHz, METHANOL-d$_4$) δ ppm 0.96 (t, J = 7.4 Hz, 3 H), 1.33-1.47 (m, 2 H), 1.60-1.73 (m, 2 H), 3.57 (t, J = 7.3 Hz, 2 H), 5.65 (s, 2 H), 8.20 (dd, J = 7.9, 5.9 Hz, 1 H), 8.86 (d, J = 7.8 Hz, 1 H), 8.92 (d, J = 5.5 Hz, 1 H), 9.17 (s, 1 H) exchangeable protons not seen. | D, 4.34 | 275 |
| 22 | 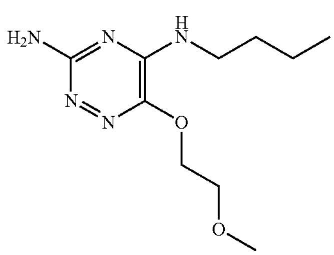 [SMILES: CCCCNc1nc(N)nnc1OCCOC] | $^1$H NMR (400 MHz, METHANOL-d$_4$) δ ppm 0.97 (t, J = 7.4 Hz, 3 H), 1.34-1.45 (m, 2 H), 1.65 (t, J = 7.4 Hz, 2 H), 3.54 (t, J = 7.3 Hz, 2 H), 3.79 (dd, J = 5.3, 3.5 Hz, 2 H), 4.40-4.47 (m, 2 H) exchangeable protons not seen. | D, 3.99 | 242 |
| 23 | 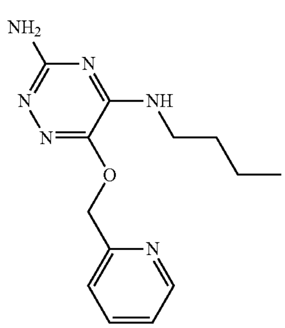 [SMILES: CCCCNc1nc(N)nnc1OCc1ccccn1] | $^1$H NMR (400 MHz, METHANOL-d$_4$) δ ppm 0.98 (t, J = 7.4 Hz, 3 H), 1.42 (dd, J = 15.1, 7.3 Hz, 2 H), 1.64 (quin, J = 7.4 Hz, 2 H), 3.40-3.52 (m, 2 H), 4.62 (br. s., 2 H), 4.81 (br. s., 1 H), 5.41-5.53 (m, 2 H), 7.34-7.47 (m, 1 H), 7.60 (d, J = 7.8 Hz, 1 H), 7.89 (td, J = 7.8, 1.8 Hz, 1 H), 8.57 (d, J = 4.5 Hz, 1 H) | A, 2.91 | 275 |

TABLE I-continued

Compounds of formula (I). The following compounds were synthesized according to one of the methods described above.

| # | STRUCTURE | H NMR | LC Method, Retention Time (min) | Mass Found (M + H) |
|---|---|---|---|---|
| 24 | 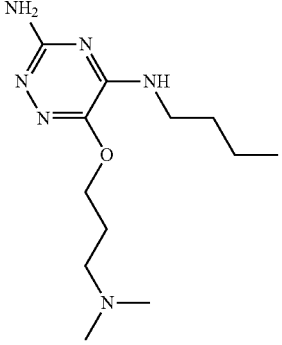 [SMILES: CCCCNc1nc(N)nnc1OCCCN(C)C] | $^1$H NMR (400 MHz, METHANOL-d$_4$) δppm 1.00 (t, J = 7.4 Hz, 3 H), 1.34-1.51 (m, 2 H), 1.70 (t, J = 7.3 Hz, 2 H), 2.31 (dd, J = 10.0, 5.5 Hz, 2 H), 2.89-3.00 (m, 6 H), 3.39-3.47 (m, 2 H), 3.59 (t, J = 7.4 Hz, 2 H), 4.44 (t, J = 5.8 Hz, 2 H), exchangeable protons not observed. | D, 4.6 | 269 |

Analytical Methods.

All compounds were characterized by LC-MS according to the following LC-MS methods.

Method A

| Column | YMC-PACK ODS-AQ, 50 × 2.0 mm 5 μm | | |
|---|---|---|---|
| Mobile Phase | A: H$_2$O (0.1%TFA) B: CH$_3$CN (0.05%TFA) | | |
| | TIME(min) | A% | B% |
| | 0 | 100 | 0 |
| | 1 | 100 | 0 |
| | 5 | 40 | 60 |
| | 7.5 | 40 | 60 |
| | 8 | 100 | 0 |
| Flow Rate | 0.8 mL/min | | |
| Wavelength | UV 220 nm | | |
| Column Temperture | 50° C. | | |
| MS polarity | positive | | |
| LC-MS | Agilent 1100 | | |

Method B.

Reversed phase UPLC on Waters Acquity BEH (bridged ethylsiloxane/silica hybrid) C18 column (1.7 μm, 2.1×100 mm) with a flow rate of 0.343 mL/min. Two mobile phases (mobile phase A: 95% 7 mM ammonium acetate/5% acetonitrile; mobile phase B: 100% acetonitrile) were employed to run a gradient condition from 84.2% A and 15.8% B (hold for 0.49 minutes) to 10.5% A and 89.5% B in 2.18 minutes, hold for 1.94 min and back to the initial conditions in 0.73 min, hold for 0.73 minutes. An injection volume of 2 μL was used. Cone voltage was 20V for positive and negative ionization mode. Mass spectra were acquired by scanning from 100 to 1000 in 0.2 seconds using an interscan delay of 0.1 seconds.

Method C

| Column | YMC-PACK ODS-AQ, 50 × 2.0 mm 5 μm | | |
|---|---|---|---|
| Mobile Phase | A: H$_2$O (0.1%TFA) B: CH$_3$CN (0.05%TFA) | | |
| | TIME(min) | A% | B% |
| | 0 | 90 | 10 |
| | 0.8 | 90 | 10 |
| | 4.5 | 20 | 80 |
| | 7.5 | 20 | 80 |
| | 8 | 90 | 10 |
| Flow Rate | 0.8 mL/min | | |
| Wavelength | UV 220 nm | | |
| Oven Temperature | 50° C. | | |
| MS polarity | positive | | |
| LC-MS | Agilent 1100 | | |

Method D

| Column | Ultimate XB-C18, 50 × 2.1mm 5pm | | |
|---|---|---|---|
| Mobile Phase | C: H$_2$O (10 mmol/L NH4HCO3) D: CH$_3$CN | | |
| | TIME(min) | C% | D% |
| | 0 | 100 | 0 |
| | 1 | 100 | 0 |
| | 5 | 40 | 60 |
| | 7.5 | 40 | 60 |
| | 8 | 100 | 0 |
| Flow Rate | 0.8 mL/min | | |
| Wavelength | UV 220 nm | | |
| Oven Tem. | 50° C. | | |
| MS polarity | positive | | |
| LC-MS | Agilent 1100 | | |

Biological Activity of Compounds of Formula (I)

Description of Biological Assays

Assessment of TLR7 and TLR8 activity

The ability of compounds to activate human TLR7 and/or TLR8 was assessed in a cellular reporter assay using HEK293 cells transiently transfected with a TLR7 or TLR8 expression vector and NFκB-luc reporter construct.

Briefly, HEK293 cells were grown in culture medium (DMEM supplemented with 10% FCS and 2 mM Glutamine). For transfection of cells in 10 cm dishes, cells were detached with Trypsin-EDTA, transfected with a mix of CMV-TLR7 or TLR8 plasmid (750 ng), NFκB-luc plasmid (375 ng) and a transfection reagent and incubated overnight at 37° C. in a humidified 5% CO$_2$ atmosphere. Transfected cells were then detached with Trypsin-EDTA, washed in PBS and resuspended in medium to a density of 1.67×10$^5$ cells/mL. Thirty microliters of cells were then dispensed into each well in 384-well plates, where 10 μL of compound in 4% DMSO was already present. Following 6 hours incubation at 37° C., 5% $CO_2$, the luciferase activity was determined by adding 15 μL of Steady Lite Plus substrate (Perkin Elmer) to each well and readout performed on a ViewLux ultraHTS microplate imager (Perkin Elmer). Dose response curves were generated from measurements performed in quadruplicates. Lowest effective concentrations (LEC) values, defined as the concentration that induces an effect which is at least two fold above the standard deviation of the assay, were determined for each compound.

Compound toxicity was determined in parallel using a similar dilution series of compound with 30 μL per well of cells transfected with the CMV-TLR7 construct alone ($1.67 \times 10^5$ cells/mL), in 384-well plates. Cell viability was measured after 6 hours incubation at 37° C., 5% $CO_2$ by adding 15 μL of ATP lite (Perkin Elmer) per well and reading on a ViewLux ultraHTS microplate imager (Perkin Elmer). Data was reported as $CC_{50}$.

In parallel, a similar dilution series of compound was used (10 μL of compound in 4% DMSO) with 30 μL per well of cells transfected with NFκB-luc reporter construct alone ($1.67 \times 10^5$ cells/mL). Six hours after incubation at 37° C., 5% $CO_2$, the luciferase activity was determined by adding 15 μl of Steady Lite Plus substrate (Perkin Elmer) to each well and readout performed on a ViewLux ultraHTS microplate imager (Perkin Elmer). Counterscreen data is reported as LEC.

Activation of ISRE Promoter Elements

The potential of compounds to induce IFN-I was also evaluated by measuring the activation of interferon-stimulated responsive elements (ISRE) by conditioned media from PBMC. The ISRE element of sequence GAAACTGAAACT is highly responsive to the STAT1-STAT2-IRF9 transcription factor, activated upon binding of IFN-I to their receptor IFNAR (Clontech, PT3372-5W). The plasmid pISRE-Luc from Clontech (ref. 631913) contains 5 copies of this ISRE element, followed by the firefly luciferase ORF. A HEK293 cell line stably transfected with pISRE-Luc (HEK-ISREluc) was established to profile of the conditioned PBMC cell culture media.

Briefly, PBMCs were prepared from buffy coats of at least two donors using a standard Ficoll centrifugation protocol. Isolated PBMCs were resuspended in RPMI medium supplemented with 10% human AB serum and $2 \times 10^5$ cells/well were dispensed into 384-well plates containing compounds (70 μL total volume). After overnight incubation, 10 μL of supernatant was transferred to 384-well plates containing $5 \times 10^3$ HEK-ISREluc cells/well in 30 μL (plated the day before). Following 24 hours of incubation, activation of the ISRE elements was measured by assaying luciferase activity using 40 μL/well Steady Lite Plus substrate (Perkin Elmer) and measured with ViewLux ultraHTS microplate imager (Perkin Elmer). The stimulating activity of each compound on the HEK-ISREluc cells was reported as LEC value, defined as the compound concentration applied to the PBMCs resulting in a luciferase activity at least two fold above the standard deviation of the assay. The LEC in turn indicates the degree of ISRE activation on transfer of a defined amount of PBMC culture medium. Recombinant interferon α-2a (Roferon-A) was used as a standard control compound.

TABLE II

BIOLOGICAL ACTIVITY.

| # | STRUCTURE | Human TLR 7 (LEC) μM | Human TLR 8 (LEC) μM | HEK-ISRE luc (LEC) μM |
|---|---|---|---|---|
| 8 | 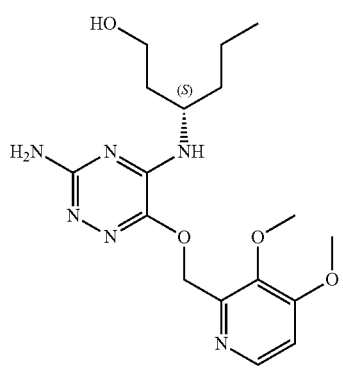 | 0.24 | 0.56 | 0.014 |
| 12 | 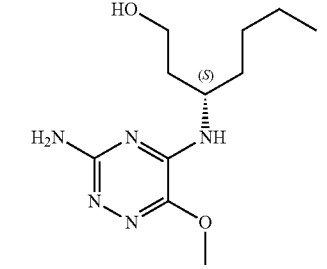 | 7.8 | 5.87 | 2.72 |

TABLE II-continued
BIOLOGICAL ACTIVITY.
| # | STRUCTURE | Human TLR 7 (LEC) μM | Human TLR 8 (LEC) μM | HEK-ISRE luc (LEC) μM |
|---|---|---|---|---|
| 15 | 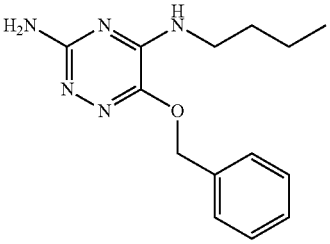 | 2.94 | 1.93 | 1.85 |
| 16 | 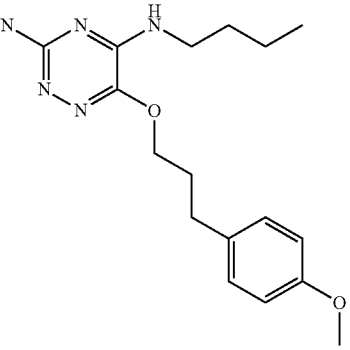 | 0.38 | 0.81 | 0.14 |
| 17 | 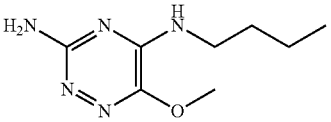 | 17.49 | 2.04 | 1.02 |
| 18 | 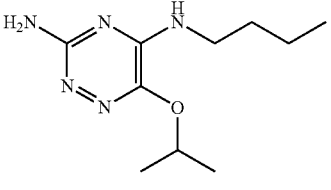 | 8.27 | 0.46 | 0.53 |
| 19 | 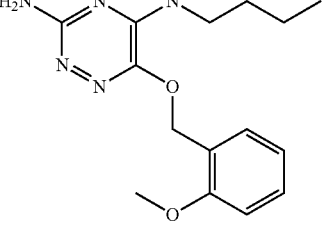 | 0.66 | 0.64 | 0.43 |
| 20 | 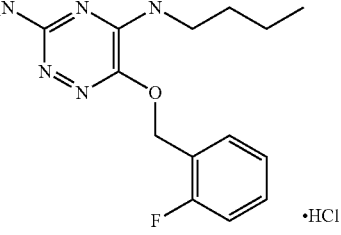 | 0.75 | 0.56 | 0.54 |

TABLE II-continued

BIOLOGICAL ACTIVITY.

| # | STRUCTURE | Human TLR 7 (LEC) μM | Human TLR 8 (LEC) μM | HEK-ISRE luc (LEC) μM |
|---|---|---|---|---|
| 21 | (structure) •HCl | 1.71 | 0.59 | 0.14 |
| 22 | (structure) •HCl | 4.75 | 1.0 | 0.41 |
| 23 | (structure) | 0.17 | 0.33 | 0.14 |
| 24 | (structure) •HCl | >25 | 0.1 | 0.17 |

All compounds showed no toxicity up to the highest tested concentration. All compounds showed no activity (LEC>25 μM) in the HEK 293 NF-kB counterscreen assay described above.

The invention claimed is:

1. A compound of formula (I)

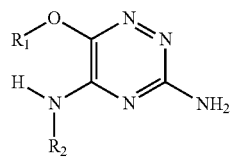

or a pharmaceutically acceptable salt, tautomer(s), or solvate thereof, wherein:

$R_1$ is $C_{1-6}$alkyl, arylalkyl, or heteroarylalkyl each of which is optionally substituted by one or more substituents independently selected from halogen, hydroxyl, amino, $C_{1-6}$ alkyl, di-($C_{1-6}$)alkylamino, $C_{1-6}$ alkylamino, $C_{1-6}$ alkoxy, $C_{3-6}$ cycloalkyl, carboxylic acid, carboxylic ester, carboxylic amide, heterocycle, aryl, alkenyl, alkynyl, arylalkyl, heteroaryl, heteroarylalkyl, and nitrile, and $R_2$ is $C_{1-8}$ alkyl, optionally substituted by one or more substituents independently selected from halogen, hydroxyl, amino, $C_{1-3}$ alkyl, $C_{1-3}$ alkoxy, $C_{3-6}$ cycloalkyl, carboxylic acid, carboxylic ester, carboxylic amide, di-($C_{1-6}$)alkylamino, $C_{1-6}$ alkylamino, aryl, heteroaryl, heteroarylalkyl and nitrile.

2. The compound according to claim 1 wherein $R_2$ is butyl or pentyl and wherein $R_1$ is $C_{1-6}$alkyl, arylalkyl, heteroarylalkyl each of which is optionally substituted by one or more substituents independently selected from halogen, hydroxyl, amino, $C_{1-6}$ alkyl, di-($C_{1-6}$)alkylamino, $C_{1-6}$ alkylamino, $C_{1-6}$ alkoxy, $C_{3-6}$ cycloalkyl, carboxylic acid, carboxylic ester, carboxylic amide, heterocycle, di-($C_{1-6}$)alkylamino, $C_{1-6}$ alkylamino, aryl, alkenyl, alkynyl, arylalkyl, heteroaryl, heteroarylalkyl and nitrile.

3. The compound according to claim 1 wherein $R_2$ is $C_{1-8}$ alkyl substituted with hydroxyl, and wherein $R_1$ is a substituted or unsubstituted arylalkyl group.

4. The compound according to claim 1 wherein $R_1$ is an arylalkyl and $R_2$ is $C_{1-8}$ alkyl substituted with a hydroxyl, or one of the following examples in any stereochemical configuration:

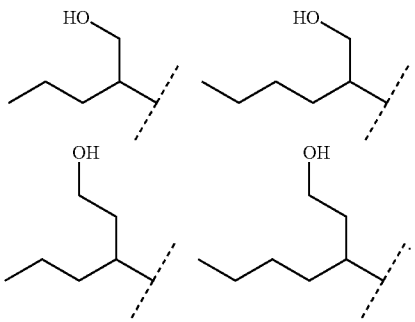

5. The compound according to claim 1 wherein $R_1$ is $CH_3$ and wherein $R_2$ is $C_{1-8}$ alkyl, optionally substituted by one or more substituents independently selected from halogen, hydroxyl, amino, $C_{1-3}$ alkyl, $C_{1-3}$ alkoxy, $C_{3-6}$ cycloalkyl, carboxylic acid, carboxylic ester, carboxylic amide, di-($C_{1-6}$) alkylamino, $C_{1-6}$ alkylamino, aryl, heteroaryl, heteroarylalkyl and nitrile.

6. The compound according to claim 1 wherein $R_1$ is a heteroarylalkyl, and wherein $R_2$ is $C_{1-8}$ alkyl, optionally substituted by one or more substituents independently selected from halogen, hydroxyl, amino, $C_{1-3}$ alkyl, $C_{1-3}$ alkoxy, $C_{3-6}$ cycloalkyl, carboxylic acid, carboxylic ester, carboxylic amide, di-($C_{1-6}$)alkylamino, $C_{1-6}$ alkylamino, aryl, heteroaryl, heteroarylalkyl and nitrile.

7. A pharmaceutical composition comprising a compound of formula (I) or a pharmaceutically acceptable salt, tautomer(s), or solvate thereof according to claim 1 together with one or more pharmaceutically acceptable excipients, diluents or carriers.

* * * * *